US012008756B2

(12) United States Patent
Bernard et al.

(10) Patent No.: US 12,008,756 B2
(45) Date of Patent: Jun. 11, 2024

(54) METHOD AND DEVICE FOR DETERMINING A MINIMUM VALUE OF LASER ENERGY NECESSARY FOR THE FORMATION OF A GAS BUBBLE

(71) Applicant: KERANOVA, Saint Etienne (FR)

(72) Inventors: Aurelien Bernard, Saint Etienne (FR); Emmanuel Baubeau, Saint Etienne (FR)

(73) Assignee: KERANOVA, Saint Etienne (FR)

( * ) Notice: Subject to any disclaimer, the term of this patent is extended or adjusted under 35 U.S.C. 154(b) by 501 days.

(21) Appl. No.: 17/275,294

(22) PCT Filed: Sep. 20, 2019

(86) PCT No.: PCT/EP2019/075280
§ 371 (c)(1),
(2) Date: Mar. 11, 2021

(87) PCT Pub. No.: WO2020/058459
PCT Pub. Date: Mar. 26, 2020

(65) Prior Publication Data
US 2022/0101528 A1    Mar. 31, 2022

(30) Foreign Application Priority Data

Sep. 20, 2018   (FR) ...................................... 1858534

(51) Int. Cl.
*G06K 9/00*       (2022.01)
*G06T 7/00*       (2017.01)
*A61F 9/008*      (2006.01)

(52) U.S. Cl.
CPC ........ *G06T 7/0014* (2013.01); *A61F 9/00825* (2013.01); *A61F 2009/00851* (2013.01);
(Continued)

(58) Field of Classification Search
CPC .................. A61F 9/008; A61F 9/00825; A61F 2009/00851; A61F 2009/0087;
(Continued)

(56) References Cited

U.S. PATENT DOCUMENTS

2009/0137993 A1\* 5/2009 Kurtz .................. A61F 9/00825
606/6
2012/0259321 A1   10/2012 Vera et al.
(Continued)

FOREIGN PATENT DOCUMENTS

CN    106176035 A    12/2016
CN    107530195 A     1/2018
(Continued)

OTHER PUBLICATIONS

First Office Action issued by China National Intellectual Property Administration dated Dec. 12, 2022, during the prosecution of corresponding chinese application No. 201980059168.0, accompanied by the English translation of the same.

*Primary Examiner* — Atiba O Fitzpatrick
(74) *Attorney, Agent, or Firm* — BCF LLP (57) ABSTRACT

The invention concerns a method for determining a minimum value of L.A.S.E.R. energy necessary to form, by using a LASER source, a gas bubble in an ocular tissue, the method comprising:
  acquisition (200) of a reference image,
  emission (210) at a sampling point, of a L.A.S.E.R. beam,
  acquisition (220) of one (or more) current image(s) of the ocular tissue,
  detection (230) of one (or more) gas bubble(s) by comparing the current image(s) and the reference image,
  determination (240, 250) of the minimum value based on the detected gas bubble(s).

17 Claims, 5 Drawing Sheets

(52) U.S. Cl.
CPC ............... *G06T 2207/10101* (2013.01); *G06T 2207/30041* (2013.01)

(58) Field of Classification Search
CPC .. A61F 2009/00872; A61F 2009/00887; A61F 2009/00855; G06T 2207/10101; G06T 2207/30041; G06T 7/0014; A61B 3/102
See application file for complete search history.

(56) References Cited

U.S. PATENT DOCUMENTS

| | | |
|---|---|---|
| 2014/0128853 A1 | 5/2014 | Angeley et al. |
| 2014/0188093 A1* | 7/2014 | Kurtz ..................... A61F 9/009 606/4 |
| 2015/0209184 A1 | 7/2015 | Goldshleger et al. |
| 2016/0325375 A1 | 11/2016 | Lemonis |
| 2016/0367399 A1* | 12/2016 | Goldshleger ......... A61F 9/0084 |

FOREIGN PATENT DOCUMENTS

| | | |
|---|---|---|
| RU | 2009-137641 A | 4/2011 |
| WO | 2015/069197 A1 | 11/2014 |

\* cited by examiner

METHOD AND DEVICE FOR DETERMINING A MINIMUM VALUE OF LASER ENERGY NECESSARY FOR THE FORMATION OF A GAS BUBBLE

CROSS-REFERENCE TO RELATED APPLICATIONS

This application is a national phase filing under 35 U.S.C. § 371 of International Application No. PCT/EP2019/075280 filed on Sep. 20, 2019, which claims benefit of priority from French Patent Application No. 1858534 filed Sep. 20, 2018, the contents of which are hereby incorporated by reference in their entirety.

TECHNICAL FIELD

The present invention concerns the technical field of surgical operations performed with femtosecond laser, and more particularly the field of ophthalmological surgery, in particular for corneas or lenses cutting applications.

The invention concerns a device for cutting a human or an animal tissue, such as a cornea or a lens, by means of a femtosecond laser.

By femtosecond laser is meant a light source able to emit a L.A.S.E.R. beam in the form of ultra-short pulses, the duration of which is comprised between 1 femtosecond and 100 picoseconds, preferably comprised between 1 and 1,000 femtoseconds, in particular approximately a hundred femtoseconds.

PRIOR ART

The femtosecond lasers are commonly used in surgery for cutting the cornea or the lens. They deliver ultra-short and high-power pulses.

During a lens surgery, the femtosecond laser can be used to perform a cut of the corneal tissue, by focusing a L.A.S.E.R. beam in the lens. More specifically, with each pulse, the femtosecond laser generates a beam. This beam is focused (at a so-called "focusing" point) located in the lens. A gas bubble is formed at the focusing point, causing a very localized disruption of the surrounding tissues.

Part of the energy of the beam is consumed during the generation of the gas bubble. The rest of the energy of the beam propagates up to the retina, causing a local heating of the retina, which could generate an injury.

In order to limit local heating of the retina, it is therefore preferable that the energy of the beam does not exceed the minimum energy necessary for the formation of a gas bubble.

It is very difficult to determine this minimum energy necessary for the formation of a gas bubble by using only preoperative data. Indeed, the amount of energy necessary for the formation of a gas bubble in the lens depends on numerous factors such as:
- the inhomogeneities of the lens, particularly of the cataractous lens where transparency is reduced heterogeneously (the lens can be more or less opaque in some places),
- the scattering of the L.A.S.E.R. beam during its propagation,
- the inhomogeneities in quality of the L.A.S.E.R. beam due to imperfections of the optical elements.

The current methods, aiming at cutting by means of a femtosecond L.A.S.E.R. an ocular tissue such as a cataractous human lens, implement empirical means for determining the energy necessary to obtain an optimal result. It is therefore common that the energy used is not suitable at all points of the tissue to be cut and that the energy is too high or not high enough, which results respectively in the formation of too large gas bubbles or in the lack of efficiency. The formation of too large gas bubbles can result in the rupture of the capsular bag, which is major surgical complication, or in the lack of efficiency of the completion of the cut due to the reduction in the efficiency of the laser because of the bubble curtain that can be formed. The lack of efficiency when the energy is not high enough obliges the surgeon to use ultrasound longer in order to complete the fragmentation of the cataractous lens.

It is therefore necessary to develop a non-empirical method which determines at each point of the tissue to be cut, the optimum energy level allowing obtaining an effective treatment with an optimum level of safety.

One aim of the present invention is therefore to propose a method and an associated device for determining a minimum value of L.A.S.E.R. energy necessary to form a gas bubble in one (or more) elementary area(s) of an ocular tissue.

DISCLOSURE OF THE INVENTION

To this end, the invention proposes a method for determining a minimum value of L.A.S.E.R. energy necessary to form, by using a cutting apparatus including a femtosecond L.A.S.E.R. source, a gas bubble in at least one elementary area extending in a cutting plane of an ocular tissue, remarkable in that the method comprises the following steps:
  a) Receiving by a data processing unit a reference image of the ocular tissue, said reference image having been acquired by an imaging system prior to the emission of a plurality of L.A.S.E.R. beams able to focus at least at one sampling point of each elementary area, each L.A.S.E.R. beam having a respective energy different from the other L.A.S.E.R. beams of the plurality of L.A.S.E.R. beams,
  b) Receiving by the data processing unit at least one current image of the ocular tissue, each current image having been acquired by the imaging system subsequently to the emission of at least one L.A.S.E.R. beam of the plurality of L.A.S.E.R. beams,
then for each elementary area, implementing the following steps by the data processing unit:
  c) Detecting by comparing the reference image with each current image, at least one gas bubble formed in the elementary area, each gas bubble being associated with a respective L.A.S.E.R. beam,
  d) Determining based on the at least one detected gas bubble, a minimum value of energy necessary for the formation of a gas bubble in the elementary area.

Preferred but non-limiting aspects of the method according to the invention are as follows:
  the reference and current images can be OCT images, the detection step comprising, for each current image, the sub-steps consisting in:
    calculating at each sampling point, an intensity variation of backscattered light received by the imaging system between the pixels of the current image and the pixels of the reference image,
    comparing this calculated intensity variation with a threshold value to identify the formation of a gas bubble if the calculated intensity variation is greater than the threshold value;

for each elementary area, each L.A.S.E.R. beam may be able to focus at a single sampling point of the elementary area, the receiving step b) consisting in receiving a plurality of current images of the ocular tissue, each current image having been acquired by the imaging system subsequently to the emission of a respective L.A.S.E.R. beam in each elementary area;

the determination step can include the following sub-steps for each elementary area:
if a single gas bubble is detected:
assigning to the minimum value a multiple k of the energy of the L.A.S.E.R. beam having induced the formation of the detected gas bubble, k being a decimal number comprised between 1 and 2,
if several gas bubbles are detected:
selecting among the current images in which a gas bubble is detected, the current image associated with the L.A.S.E.R. beam of lowest energy, and
assigning to the minimum value a multiple k of the energy of the L.A.S.E.R. beam associated with the selected current image, k being a decimal number comprised between 1 and 2;

for each elementary area, each L.A.S.E.R. beam may be able to focus at a respective sampling point of the elementary area, the receiving step b) consisting in receiving a current image of the ocular tissue, said current image having been acquired by the imaging system subsequently to the emission of the plurality of L.A.S.E.R. beams at a respective sampling point of each elementary area;

the determination step can include the following sub-steps for each elementary area:
if a single gas bubble is detected:
assigning to the minimum value a multiple k of the energy of the L.A.S.E.R. beam associated with the sampling point at which the gas bubble is detected, k being a decimal number comprised between 1 and 2,
if several gas bubbles are detected:
selecting among the sampling points at each of which a gas bubble is detected, the sampling point associated with the L.A.S.E.R. beam of lowest energy, and
assigning to the minimum value a multiple k of the energy of the L.A.S.E.R. beam associated with said selected sampling point, k being a decimal number comprised between 1 and 2;

the method can also comprise the following step:
e) recording by the data processing unit the minimum value determined for each elementary area in a storage unit;

the ocular tissue can comprise a set of elementary areas extending in a plurality of cutting planes each containing at least one elementary area, the method comprising the reiteration of steps a) to e) for each cutting plane in order to determine a three-dimensional map of the minimum values of energy necessary for the formation of gas bubbles in the set of the elementary areas of the ocular tissue.

The invention also concerns a device for determining a minimum value of L.A.S.E.R. energy necessary to form, by using a cutting apparatus including a femtosecond L.A.S.E.R. source, a gas bubble in at least one elementary area extending in a cutting plane of an ocular tissue, the determination device including an imaging system for the acquisition of images, remarkable in that the determination device further comprises a data processing unit including means for:

a) Receiving a reference image of the ocular tissue, said reference image having been acquired by the imaging system prior to the emission of a plurality of L.A.S.E.R. beams able to focus at least at one sampling point of each elementary area, each L.A.S.E.R. beam having a respective energy different from the other L.A.S.E.R. beams of the plurality, b) Receiving at least one current image of the ocular tissue, each current image having been acquired by the imaging system subsequently to the emission of at least one L.A.S.E.R. beam of the plurality of L.A.S.E.R. beams, then for each elementary area:
c) Detecting by comparing the reference image with each current image, at least one gas bubble formed in the elementary area, each gas bubble being associated with a respective L.A.S.E.R. beam, d) Determining, based on the at least one gas bubble, a minimum value of energy necessary for the formation of a gas bubble in the elementary area.

Preferred but non-limiting aspects of the device according to the invention are as follows:

the reference and current images can be OCT images, the data processing unit including means for detecting at least one gas bubble by, for each current image:
calculating at each sampling point, an intensity variation of backscattered light received by the imaging system between the pixels of the current image and the pixels of the reference image,
comparing this calculated intensity variation with a threshold value to identify the formation of a gas bubble if the calculated intensity variation is greater than the threshold value;

for each elementary area, each L.A.S.E.R. beam may be able to focus at a single sampling point of the elementary area, the data processing unit including means for receiving a plurality of current images of the ocular tissue, each current image having been acquired by the imaging system subsequently to the emission of a respective L.A.S.E.R. beam in each elementary area;

the data processing unit can include means for determining a minimum value by, for each elementary area:
if a single gas bubble is detected:
assigning to the minimum value a multiple k of the energy of the L.A.S.E.R. beam having induced the formation of the detected gas bubble, k being a decimal number comprised between 1 and 2,
if several gas bubbles are detected:
selecting among the current images in which a gas bubble is detected, the current image associated with the L.A.S.E.R. beam of lowest energy, and
assigning to the minimum value a multiple k of the energy of the L.A.S.E.R. beam associated with the selected current image, k being a decimal number comprised between 1 and 2;

for each elementary area, each L.A.S.E.R. beam may be able to focus at a respective sampling point of the elementary area, the processing unit including means for receiving a current image of the ocular tissue, said current image having been acquired by the imaging system subsequently to the emission of the plurality of L.A.S.E.R. beams at a respective sampling point of each elementary area;

the data processing unit can include means for determining a minimum value by, for each elementary area:
if a single gas bubble is detected:
assigning to the minimum value a multiple k of the energy of the L.A.S.E.R. beam associated with the sampling point at which the gas bubble is detected, k being a decimal number comprised between 1 and 2,
if several gas bubbles are detected:
selecting among the sampling points at each of which a gas bubble is detected, the sampling point associated with the L.A.S.E.R. beam of lowest energy, and
assigning to the minimum value a multiple k of the energy of the L.A.S.E.R. beam associated with said selected sampling point, k being a decimal number comprised between 1 and 2;
the processing unit can also include means for:
e) recording the minimum value determined for each elementary area in a storage unit;
the ocular tissue can comprise a set of elementary areas extending in a plurality of cutting planes each containing at least one elementary area, the processing unit further includes means for reiterating steps a) to e) for each cutting plane in order to determine a three-dimensional map of the minimum values of energy necessary for the formation of gas bubbles in the set of the elementary areas of the ocular tissue.

The invention also concerns a method for determining a minimum value of L.A.S.E.R. energy necessary to form, by using a cutting apparatus including a femtosecond L.A.S.E.R. source, a gas bubble in at least an elementary area of an ocular tissue, remarkable in that the method comprises the following steps:
a) Receiving by a data processing unit, a reference image of the ocular tissue, said reference image having been acquired by an imaging system prior to the emission of a L.A.S.E.R. beam able to focus at a respective sampling point of each elementary area,
b) Receiving by the data processing unit at least one current image of the ocular tissue, said current image having been acquired by the imaging system subsequently to the emission of the L.A.S.E.R. beam,
c) Searching by the data processing unit for at least one gas bubble formed at the sampling point of each elementary area, by comparing the current and reference images,
d) Assigning the energy of the L.A.S.E.R. beam to the minimum value associated with each elementary area in which a bubble is detected,
e) Increasing the energy of the L.A.S.E.R. beam and reiterating steps b) to e) for each elementary area in which no bubble is detected.

Preferred but non-limiting aspects of the method according to the invention are as follows:
the reference and current images can be OCT images, the searching step comprising the sub-steps consisting in:
calculating at the sampling point, an intensity variation of reflected light received by the imaging system between the pixels of the current image and the pixels of the reference image,
comparing this calculated intensity variation with a threshold value to identify the formation of a gas bubble at the sampling point if the calculated intensity variation is greater than the threshold value;
the method can further comprise the following step:
f) recording by the data processing unit the minimum value associated with each elementary area in a storage unit
the ocular tissue can comprise a set of elementary areas extending in a plurality of cutting planes each containing at least one elementary area, the method comprising the reiteration of steps a) to f) for each cutting plane in order to determine a three-dimensional map of the minimum values of energy necessary for the formation of gas bubbles in the set of the elementary areas of the ocular tissue.

The invention also concerns a device for determining a minimum value of L.A.S.E.R. energy necessary to form, by using a cutting apparatus including a femtosecond L.A.S.E.R. source, a gas bubble in at least one elementary area of an ocular tissue, the determination device including an imaging system for the acquisition of images, remarkable in that the determination device further comprises a data processing unit adapted to:
a) Receive a reference image of the ocular tissue, said reference image having been acquired by the imaging system prior to the emission of a L.A.S.E.R. beam able to focus at a respective sampling point of each elementary area,
b) Receive at least one current image of the ocular tissue, said current image having been acquired by the imaging system subsequently to the emission of the L.A.S.E.R. beam,
c) Search for at least one gas bubble formed at the sampling point of each elementary area, by comparing the current and reference images,
d) Assign the energy of the L.A.S.E.R. beam to the minimum value associated with each elementary area in which a bubble is detected,
e) Increase the energy of the L.A.S.E.R. beam and reiterate steps b) to e) for each elementary area in which no bubble is detected.

Preferred but non-limiting aspects of the device according to the invention are as follows:
the reference and current images can be OCT images, the data processing unit being adapted to search for at least one gas bubble by:
calculating at the sampling point, an intensity variation of reflected light received by the imaging system between the pixels of the current image and the pixels of the reference image,
comparing this calculated intensity variation with a threshold value to identify the formation of a gas bubble at the sampling point if the calculated intensity variation is greater than the threshold value;
the data processing unit can further be adapted to:
f) record the minimum value determined for the elementary area in a storage unit;
the ocular tissue can comprise a set of elementary areas extending in a plurality of cutting planes each containing at least one elementary area, the data processing unit being further adapted to reiterate steps a) to f) for each cutting plane in order to determine a three-dimensional map of the minimum values of energy necessary for the formation of gas bubbles in the set of the elementary areas of the ocular tissue.

BRIEF DESCRIPTION OF THE DRAWINGS

Other characteristics and advantages of the invention will emerge clearly from the description which is given below, by way of indication and without limitation, with reference to the appended figures, in which.

DETAILED DISCLOSURE OF THE INVENTION

The invention concerns a method and a device for determining one (or more) minimum value(s) of L.A.S.E.R. energy necessary for the formation of a gas bubble in one (or more) elementary area(s) of a human or animal ocular tissue 60 by means of a cutting apparatus including a femtosecond laser.

In the remainder of the description, the invention will be described, by way of example, for the cutting of a lens, it being understood that the present invention can be applied to the determination of one (or more) minimum value(s) of energy necessary for the formation of gas bubbles in one (or more) elementary area(s) of other ocular tissues.

1. CUTTING APPARATUS

Figure 1:
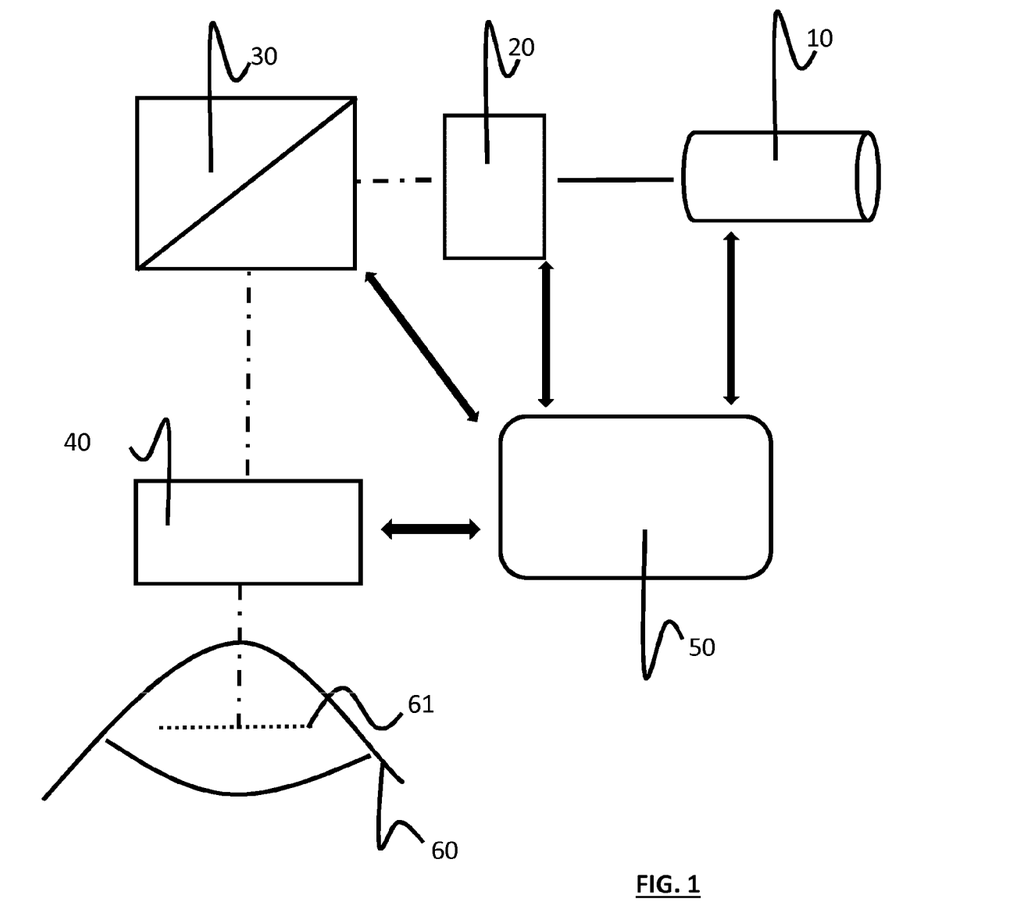
FIG. 1 is a schematic representation of an example of an apparatus for cutting an ocular tissue using a femtosecond laser.

FIG. 1 illustrates one embodiment of the cutting apparatus according to the invention. The cutting apparatus comprises:
- a femtosecond laser 10,
- an sweeping optical scanner 30 downstream of the laser 10,
- an optical focusing system 40 downstream of the sweeping optical scanner 30, and
- a control system 50 for driving the sweeping optical scanner 30 and the optical focusing system 40.

The femtosecond laser 10 is able to emit a L.A.S.E.R. beam in the form of pulses. For example, laser 10 emits a light of a 1,030 nm wavelength, in the form of pulses of 400 femtoseconds. The laser 10 has a power of 20 W and a frequency of 500 kHz.

The sweeping optical scanner 30 allows orienting the beam derived from the laser 10 to move it along a travel path set by the user in a focusing plane 61.

The optical focusing system 40 allows focusing the beam in the focusing plane 61—corresponding to the cutting plane.

The cutting apparatus may also include a shaping system 20—such as a liquid-crystal Spatial Light Modulator (SLM)—between the femtosecond laser 10 and the sweeping optical scanner 30. This shaping system 20 is positioned on the path of the beam derived from the femtosecond laser 10. The shaping system 20 allows modulating the phase of the beam from the femtosecond laser 10 in order to distribute the beam energy in a plurality of points of impact in its focal plane, this plurality of points of impact defining a pattern. More specifically, the shaping system allows, from a Gaussian L.A.S.E.R. beam generating a single point of impact, and by means of the phase mask, distributing its energy by phase modulation so as to simultaneously generate several points of impact in its focusing plane from a single L.A.S.E.R. beam shaped by phase modulation (a single beam upstream and downstream of the SLM). This generation of a plurality of points of impact from a single modulated L.A.S.E.R. beam allows (in addition to reducing the cutting time of the ocular tissue) improving the quality of the performed cut. Particularly, the shaping system allows obtaining a homogeneous cutting plane, in which the residual tissue bridges all have substantially the same dimensions (indeed, even if a portion of the modulated LASER beam is masked, the number of points of impact in the cutting plane remains identical). This improvement in the quality of the cut facilitates the dissection operation performed later by the practitioner.

The control system 50 allows driving the sweeping optical scanner 30, the possible shaping system 20 and the optical focusing system 40. The control system 50 can be composed of one (or more) work station(s), and/or one (or more) computer(s) or may be of any other type known to those skilled in the art. The control system 50 can for example comprise a mobile phone, an electronic tablet (such as an IPAD®), a Personal Digital Assistant (PDA), etc. In all cases, the control system 50 comprises a processor programmed to allow the driving of the femtosecond laser 10, the sweeping optical scanner 30, the optical focusing system 40, the shaping system 20, etc.

2. DETERMINATION DEVICE

Figure 2:
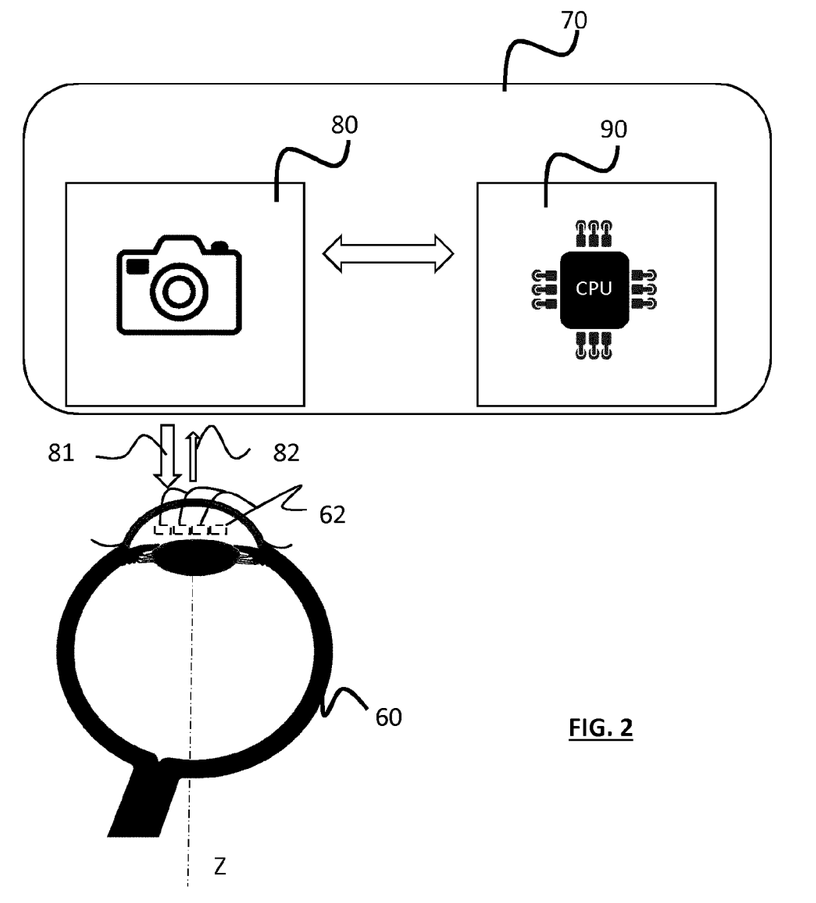
FIG. 2 is a schematic representation of a device for determining a minimum value of L.A.S.E.R. energy necessary for the formation of a gas bubble in an ocular tissue.

With reference to FIG. 2, the determination device 70 comprises:
- an imaging system 80 for acquiring OCT (Optical Coherence Tomography) type, or Scheimpflug (visible light mapping) type, or UBM (Ultrasonic Bio Microscopy) type images,
- a processing unit 90—including for example a processor and a storage unit—for processing the images acquired by the acquisition system 80 and for determining a (two-dimensional or three-dimensional) map of the minimum values of laser energy necessary for the formation of gas bubbles in a plurality of elementary areas 62 of the ocular tissue 60.

The determination device 70 can be integrated with the cutting apparatus.

In particular in a preferred embodiment:
- the processing unit 90 is part of the control system 50, and
- the acquisition system 80, the shaping system 20, the sweeping optical scanner 30 and the optical focusing system 40 are mounted in a compartment fixed to the end of a robotic arm, while the femtosecond laser 10 can be integrated into a box on which the robotic arm is fixed.

Alternatively, the determination device 70 may be remote from the cutting apparatus and comprise wired or wireless communication means (not represented) for the exchange of information between the determination device 70 and the cutting apparatus.

In all cases, the determination device 70 is programmed to implement the determination method described below.

3. DETERMINATION METHOD

3.1. General Information on the Method

The method comprises the following steps:
Acquiring a reference image of the ocular tissue to be treated,
Emitting in at least one elementary area at least two L.A.S.E.R. beams of different energies,
Acquiring at least one current image of the ocular tissue,
Comparing the current image with the reference image to detect at least one gas bubble associated with one of the L.A.S.E.R. beams,
Determining a minimum value of energy necessary for the formation of a gas bubble in the elementary area.

Each elementary area 62 can consist of a line (for example of 50 or 100 µm), a surface (of 50×50 µm or of 100×100 µm or of 1,000×1,000 µm) or an elementary volume (of 50×50×50 µm or of 100×100×100 µm or of 1,000×1,000×1,000 µm), the combination of the elementary areas allowing defining a total line, a total surface, or a total volume to be cut.

3.1.1. Acquired Images

The reference image and the current image(s) acquired by the imaging system can be of the OCT type, or of the Scheimpflug type, or of the UBM type.

One of the advantages related to the acquisition of OCT images is that an OCT-type imaging system 80 has a high sensitivity (≈100 dB) allowing obtaining high-quality images. Furthermore, the cutting apparatus integrates an OCT-type imaging system, so that no additional imaging system is needed. Finally, the OCT-type reference image can also be used to check the alignment of the cutting apparatus with the ocular tissue 60 to be treated.

For the acquisition of an OCT image, an optical beam 81 is directed towards the ocular tissue 60, and a small portion of the light 82 backscattered (by the different layers) from the ocular tissue 60 is recombined on one (or more) sensor(s) of the imaging system 80 with a reference signal. The signal recorded by the sensor(s) is modulated according to the optical path difference between the signal backscattered by the ocular tissue 60 and the reference signal. This recorded signal is used to construct the OCT image, which can be a one-dimensional image or a two-dimensional image.

More specifically, the OCT-type imaging system 80 can be used:
in "mode A" (also called "A-scan"), or
in "mode B" (also called "B-scan").

The "mode A" allows the acquisition of a one-dimensional OCT image. It is based on the emission of light information 81 (by an emitter of the imaging system) and the receipt of the interference between a backscattered light 82 (by the sensor of the imaging system) along a propagation line and the reference light: the one-dimensional OCT image obtained (from the signal recorded by the sensor) is representative of the axial backscattering profile (i.e. in depth Z) of the ocular tissue 60 at the considered point (of coordinate X, Y in the focusing plane 61).

The "mode B" allows the acquisition of a two-dimensional OCT image, by implementing a transverse scanning of the ocular tissue 60, for example along an X-direction perpendicular to the optical axis Z of the ocular tissue 60. A plurality of "mode A" backscattering profiles established for different points of the ocular tissue 60 along the X-direction is obtained. The stacking of these obtained "mode A" backscattering profiles allows constructing an OCT image in two dimensions (XZ).

3.1.2. Comparison Step

The comparison step allows detecting the possible formation of a gas bubble. Indeed, the properties of light backscattering by the ocular tissue 60 are the source of contrast of the OCT images, revealing morphological information. When a gas bubble is formed in the ocular tissue 60, it causes a variation in the backscattering properties of light by the ocular tissue 60.

The comparison step is based on the detection of the variation in the intensity of the backscattered light received by the imaging system 80 between the pixels of the current image and the pixels of the reference image. If this intensity variation is greater than a previously defined threshold value, then it is representative of the formation of a gas bubble at the point of impact of the considered L.A.S.E.R. beam. This means that the energy of the L.A.S.E.R. beam was sufficient to form a gas bubble in elementary area 62.

In order to ensure efficient cutting of the lens, the determined minimum value can be made equal to a multiple—comprised between 1 and 2 (for example 1.5× or 2×)—of the energy of the L.A.S.E.R. beam that enabled to form the detected gas bubble. It is then guaranteed that the minimum value of energy is sufficient to obtain the expected cutting effect and:
that it is unnecessary to use an energy level higher than the determined minimum value, the unnecessary extra energy being able to affect the safety of the patient,
that a lower energy level would lead to a lack of efficiency, the available energy being insufficient to obtain the formation of a gas bubble.

Different embodiments of the method can be envisaged. In particular, in first and third embodiments, the L.A.S.E.R. beams of different energies are emitted at a single sampling point in each elementary area. In a second embodiment, each L.A.S.E.R. beam of different energy is emitted at a distinct point from the elementary area, thus forming a series of adjacent points.

These different embodiments and their associated advantages are described below.

3.2. First Embodiment of the Method

In the first embodiment, the L.A.S.E.R. beams are emitted at a single sampling point for each elementary area 62 of the ocular tissue 60.

For an elementary area 62 considered, the L.A.S.E.R. beams of different—particularly increasing—energies are emitted successively at the sampling point.

A current image is acquired after each emission of a L.A.S.E.R. beam. Advantageously, when the tissue comprises several elementary areas extending in the same plane, a current image can be acquired after each emission of a L.A.S.E.R. beam at a respective sampling point of each elementary area. This allows limiting the number of acquired current images, and thus increasing the speed of the method according to the invention by limiting the time necessary for the acquisition of the current images.

After each acquisition of a current image, the latter is compared with the reference image to detect whether a gas bubble has been formed.

If a bubble has been formed, then the energy of the L.A.S.E.R. beam is sufficient to form a gas bubble: this sufficient value of energy is recorded in a storage unit and a new elementary area 62 is studied to determine the minimum value of energy necessary for the formation of a gas bubble in this new elementary area 62.

More specifically, according to this first embodiment:

a first L.A.S.E.R. beam having a first energy is emitted to focus at the sampling point of the considered elementary area 62; a first current image is acquired and compared with the reference image to detect the possible formation of a gas bubble; if a gas bubble has been formed, then the first energy is sufficient to form the gas bubble: this first energy corresponds to the minimum value of energy necessary for the formation of a gas bubble in the considered elementary area 62; a new elementary area is then studied, otherwise a second L.A.S.E.R. beam having a second energy greater than the first energy is emitted at the sampling point and a second current image is acquired to detect the formation of a possible gas bubble; if a gas bubble has been formed, then the second energy corresponds to the minimum value of energy necessary for the formation of a gas bubble in the considered elementary area; a new elementary area 62 is then studied, otherwise a third L.A.S.E.R. beam having a third energy greater than the second energy is emitted; a third current image is acquired to detect the formation of a possible gas bubble; if a gas bubble has been formed, then the third energy corresponds to the minimum value of energy necessary for the formation of a gas bubble in the considered elementary area 62; a new elementary area 62 is then studied, etc. until determining the minimum value of energy necessary for the formation of a gas bubble in the considered elementary area.

As a variant, when a single current image is acquired subsequently to the emission of a L.A.S.E.R. beam at a respective sampling point of several elementary areas extending in the same plane:

a first L.A.S.E.R. beam is emitted to focus at the sampling point of each elementary area extending in the same plane; a first current image is acquired and compared with the reference image to detect the possible formation of a gas bubble in one (or more) of the elementary areas; if a gas bubble has been formed in one (or more) of these areas, the minimum value of energy is determined for this (or these) area(s), if some areas do not contain a gas bubble, a second L.A.S.E.R. beam of higher energy is emitted at the sampling point of these some areas and a second current image is acquired to detect the formation of a possible gas bubble;

etc. until determining the minimum values in all the elementary areas extending in the same plane.

Figure 3:
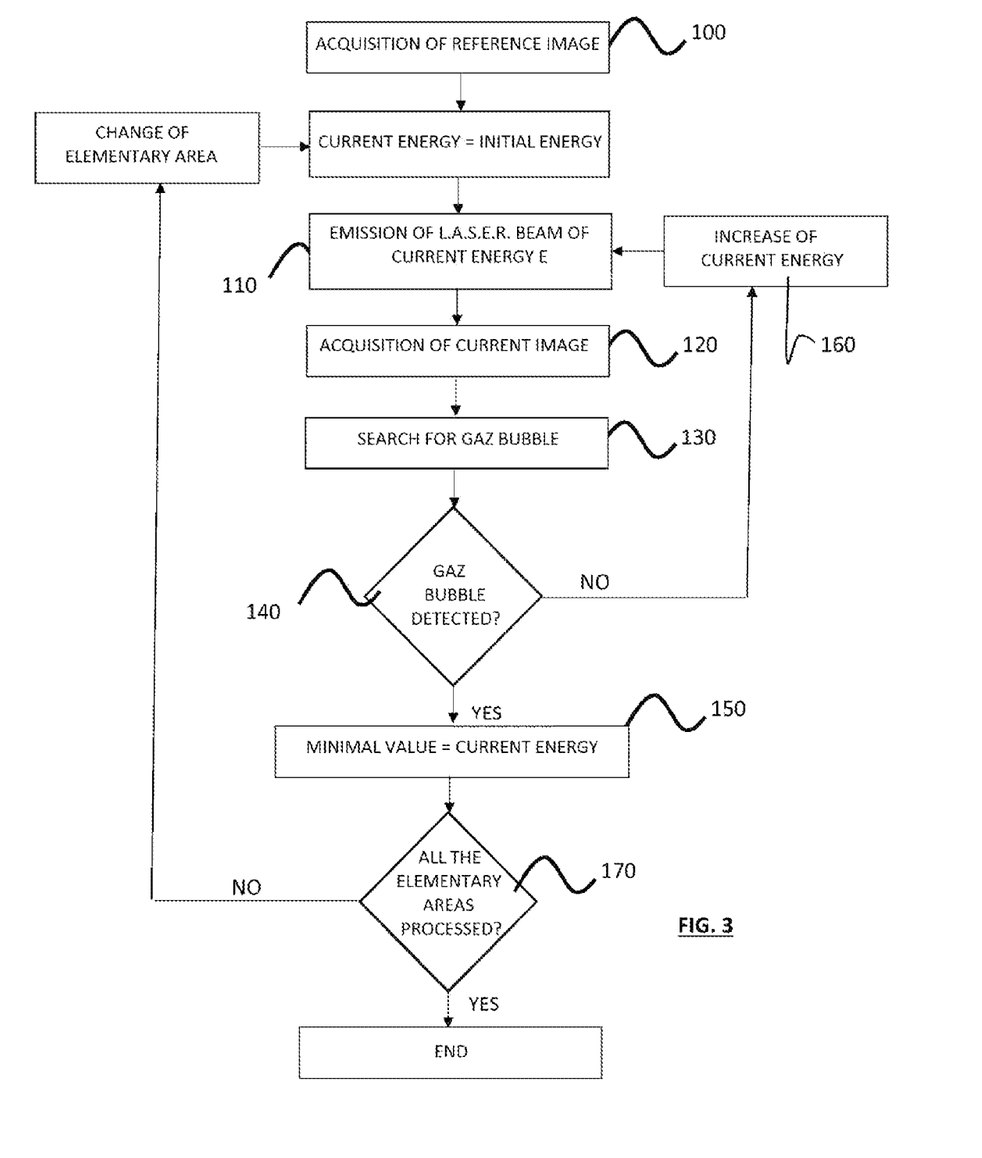
FIG. 3 is a schematic representation of a first variant of a method for determining a minimum value of L.A.S.E.R. energy necessary for the formation of a gas bubble in an ocular tissue.

Thus and as illustrated in FIG. 3, the method comprises, for each elementary area 62:

a) acquisition 100 of a reference image, b) emission 110 on the sampling point of each elementary area, of a L.A.S.E.R. beam of energy comprised between a minimum energy $E_{min}$ (assumed to be sufficient a priori to generate a gas bubble in the tissue) and a maximum energy $E_{max}$ (a multiple of $E_{min}$ (for example $E_{max}=10 \times E_{min}$))

c) acquisition 120 of a current image of the ocular tissue, said current image containing the sampling point of each elementary area, d) search 130 for a gas bubble in the current image by determining an intensity variation of the backscattered light between the reference image and the current image (for example by subtraction of the reference image from the current image) for each elementary area, e) comparison 140 of the determined energy variation in each elementary area with a threshold value, f) for each elementary area, recording 150 of the value of energy of the L.A.S.E.R. beam and of the position of the elementary area in a storage unit if the determined energy variation is greater than the threshold value, g) increase 160 of the energy of the L.A.S.E.R. beam and reiteration of steps b) to g) for each elementary area in which no bubble is detected.

Once the set of the elementary areas 62 has been processed, a mapping (in particular three-dimensional mapping) of the minimum values of energy necessary for the formation of gas bubbles in each of the elementary areas 62 of the ocular tissue 60 is obtained.

One advantage of this first embodiment concerns the fact that the L.A.S.E.R. beams of increasing energies are emitted at a single sampling point for each elementary area 62, without emission of a L.A.S.E.R. beam of energy greater than the minimum value of energy necessary for the formation of a gas bubble. However, this first embodiment is time consuming, due to the acquisition of a plurality of current images.

This is why the inventors have proposed a second embodiment of the method in which the number of acquired current images is limited to one image per elementary area 62, even one image for the set of the elementary areas 62.

3.3. Second Embodiment of the Method

In the second embodiment, the L.A.S.E.R. beams are emitted in a plurality of sampling points for each elementary area 62 of the ocular tissue 60, for example in eight points evenly spaced apart by 80 µm on a 560 µm line. More specifically for each elementary area 62, each L.A.S.E.R. beam of increasing energy is emitted (simultaneously or sequentially) at a respective sampling point.

A current image is acquired for each elementary area 62, once all the L.A.S.E.R. beams of different energies have been emitted in said elementary area 62.

The current image is compared with the reference image to detect whether one (or more) gas bubble(s) has(have) been formed. If several gas bubbles are formed, then the lowest energy that enabled to obtain a gas bubble is selected as the minimum value of energy necessary for the formation of a gas bubble.

More specifically, according to this second embodiment, first, second, third ( . . . etc.) L.A.S.E.R. beams having first, second, third increasing energies (i.e. first energy<second energy<third energy) are emitted to focus at three respective sampling points of the considered elementary area 62. A current image is acquired and compared with the reference image to detect the possible formation of gas bubbles:

if a single gas bubble has been formed at the sampling point associated with the third L.A.S.E.R. beam, then the third energy is sufficient to form the gas bubble: this third energy corresponds to the minimum value of energy necessary for the formation of a gas bubble in the considered elementary area 62; a new elementary area 62 is then studied, if several gas bubbles are formed, for example for the second and third beams, then the second energy (which is lower than the third energy) corresponds to the minimum value of energy necessary for the formation of a gas bubble in the considered elementary area 62; a new elementary area 62 is then studied.

Figure 4:
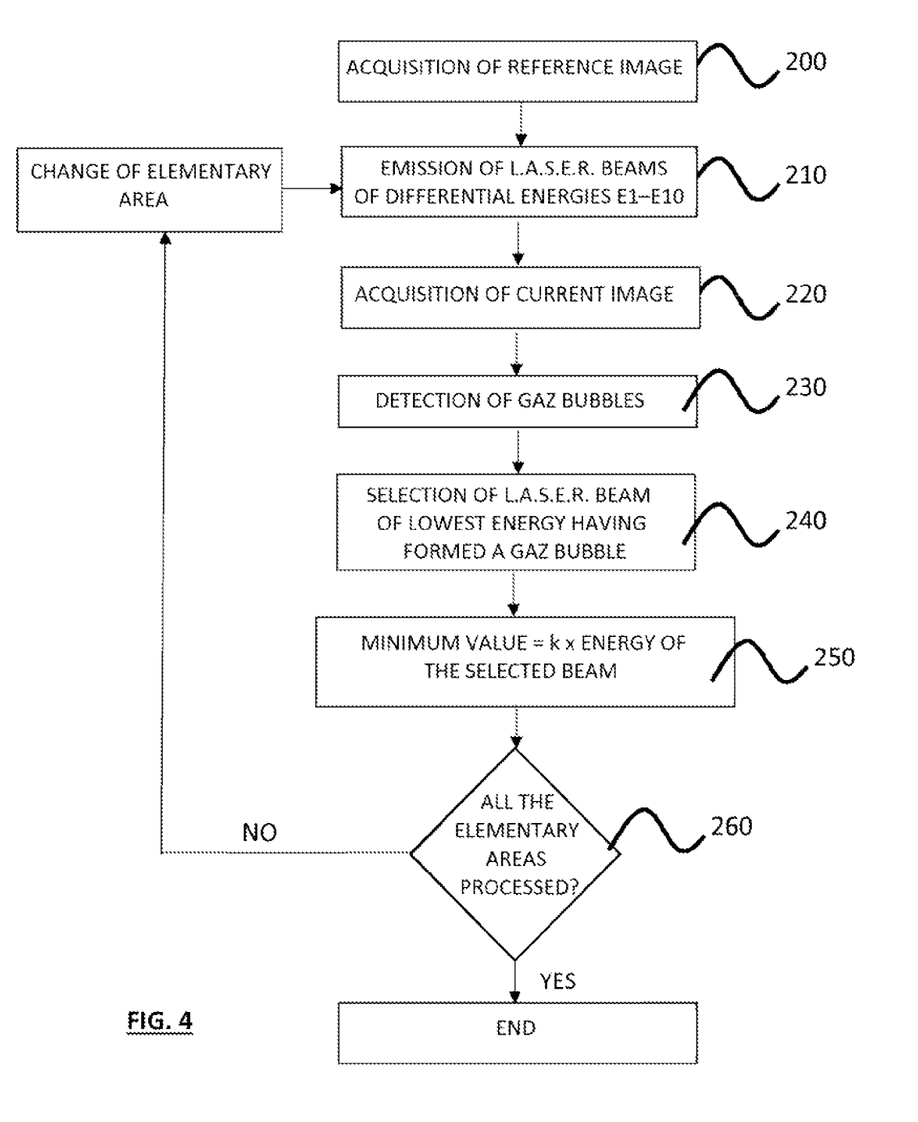
FIG. 4 is a schematic representation of a second variant of the method for determining a minimum value of L.A.S.E.R. energy necessary for the formation of a gas bubble in the ocular tissue.

Thus and as illustrated in FIG. 4, the method comprises, for each elementary area:
 a) acquisition 200 of a reference image,
 b) emission 210 on a plurality of respective sampling points, of a plurality of L.A.S.E.R. beams of different energies comprised between the minimum energy $E_{min}$ and the maximum energy $E_{max}$,
 c) acquisition 220 of a current image of the ocular tissue, said current image containing the plurality of sampling points,
 d) detection 230 of one (or more) gas bubble(s) by comparison of the current image with the reference image,
 e) selection 240 of the gas bubble associated with the L.A.S.E.R. beam of lowest energy among the set of gas bubbles,
 f) recording 250 of the value of energy of the L.A.S.E.R. beam associated with the selected gas bubble (and of the position of the elementary area) in a storage unit,
 g) if all the elementary areas have not been processed, reiteration of steps b) to g) for a new elementary area 62.

Of course, it is also possible in this embodiment to acquire a single current image for several elementary areas simultaneously (if these elementary areas are located in the same plane Bscan). In this case, the processing steps (detection of bubbles and determination of the minimum value of energy for each elementary area) can be implemented for these several elementary areas from a single current image in order to save time.

Once the set of the elementary areas 62 has been processed, a mapping (in particular three-dimensional mapping) of the minimum values of energy necessary for the formation of gas bubbles in each of the elementary areas of the ocular tissue is obtained.

As indicated previously, one advantage of this second embodiment concerns the fact that the determination of the minimum values of energy necessary for the formation of gas bubbles in each elementary area 62 is faster than with the first embodiment, given that it is necessary to carry out only one current image acquisition per studied elementary area, or even a single current image acquisition for several elementary areas extending in the same plane.

3.4. Third Embodiment of the Method

The third embodiment of the method can be considered as a combination of the first and second embodiments.

More specifically in this first embodiment, the L.A.S.E.R. beams of different—particularly increasing—energies are emitted successively at a single sampling point for each elementary area 62 of the ocular tissue 60. A current image is acquired after each emission of an L.A.S.E.R. beam on a respective sampling point of several elementary areas extending in the same plane.

For example eight L.A.S.E.R. beams of energies $E_1$ to $E_8$ are emitted successively at a respective sampling point of each elementary area extending in the same plane.

A first current image is acquired after emission of the energy beam $E_1$ at the respective sampling point of each elementary area extending in the same plane. A second current image is acquired after emission of the energy beam $E_2$ at the respective sampling point of each elementary area extending in the same plane, and so on until acquiring an eighth current image after emission of the energy beam $E_8$ at the respective sampling point of each elementary area extending in the same plane.

The eight current images are then compared with the reference image to detect the presence of a gas bubble in each elementary area. When several gas bubbles are detected for the same elementary area from several current images (for example a gas bubble is detected from the sixth, seventh and eighth current images for a considered area), then the lowest energy among the energies of the L.A.S.E.R. beams having induced the generation of a gas bubble is used to determine the minimum value necessary for the formation of a gas bubble.

Figure 5:
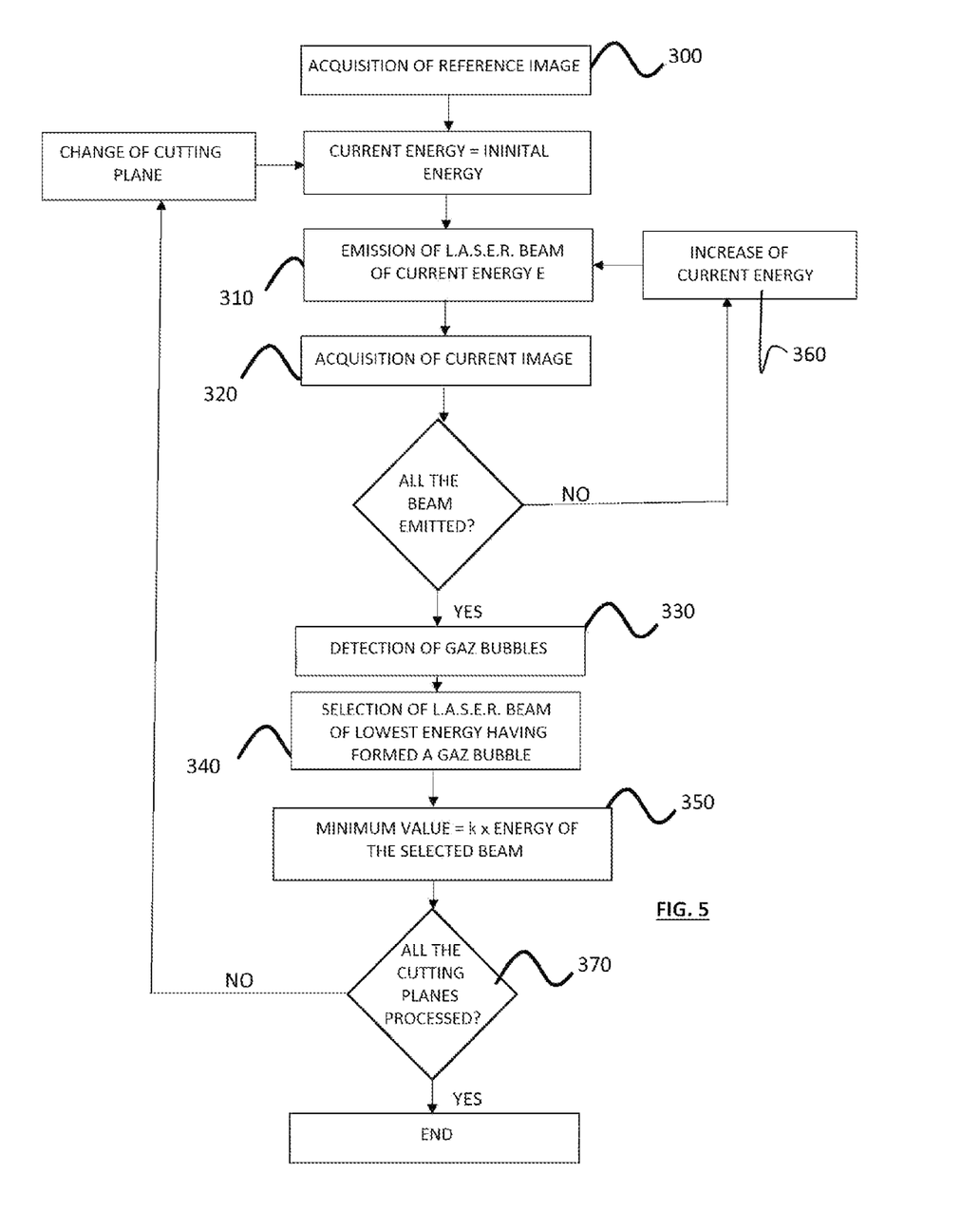
FIG. 5 is a schematic representation of a third variant of the method for determining a minimum value of L.A.S.E.R. energy necessary for the formation of a gas bubble in the ocular tissue.

Thus and as illustrated in FIG. 5, the method comprises:
 a) acquisition 300 of a reference image,
 b) emission 310 at a respective sampling point of each elementary area extending in the same plane, of a L.A.S.E.R. beam of energy comprised between a minimum energy $E_{min}$ and a maximum energy $E_{max}$,
 c) acquisition 320 of a current image of the ocular tissue, said current image containing the sampling points of the elementary areas extending in the same plane,
 d) increase 360 of the energy of the L.A.S.E.R. beam by a predetermined value and reiteration of steps b) to d) if the increased energy is lower than the maximum energy, or switching to step e) if the increased energy is greater than the maximum energy,
 e) for each elementary area extending in the same plane, detection 330 of one (or more) gas bubble(s) by comparison of the current images with the reference image,
 f) for each elementary area extending in the same plane, selection 340 of the gas bubble associated with the L.A.S.E.R. beam of lowest energy among the set of gas bubbles, and determination 350 of the minimum value of energy,
 g) for each elementary area extending in the same plane, recording of the determined value of energy (and of the position of the elementary area) in a storage unit,
 h) reiteration 370 of steps a) to g) for new elementary areas 62 extending into another plane if need be.

This embodiment allows limiting the time required for the method to determine the minimum values associated with the different elementary areas of the ocular tissue. Indeed, the steps relating to the processing of the current images can be implemented during the driving of the optical focusing system 40 to move the focusing plane 61 from one cutting plane to another.

In addition, continuing to increase the energy of the L.A.S.E.R. beam emitted on the sampling point of each elementary area even if a gas bubble has already been formed allows limiting the risks of "false positives" during detection (if a gas bubble is detected in a current image acquired subsequently to the emission of a L.A.S.E.R. beam of given energy while it is absent from the current image acquired subsequently to the emission of a L.A.S.E.R. beam of energy greater than the given energy: then this gas bubble detected constitutes a false positive).

4. CONCLUSIONS

Thus, the invention allows the determination of a minimum value of L.A.S.E.R. energy sufficient to form a gas bubble in at least one elementary area of an ocular tissue by means of a cutting apparatus including a femtosecond L.A.S.E.R source. This allows limiting the amount of excess energy of the beam likely to be propagated up to the retina in order to reduce the local heating of the retina during the implementation of the cutting operation the ocular tissue by means of the cutting device. This also allows making sure, on the contrary, that the amount of energy sent is sufficient to obtain the expected effect and thus avoiding the problems related to the lack of efficiency upon cutting the tissue resulting in an partially cut tissue.

The reader will understand that numerous modifications can be made to the invention described above without physically departing from the new teachings and advantages described here.

Consequently, all modifications of this type are intended to be incorporated within the scope of the appended claims.

The invention claimed is:

1. A method for causing a femtosecond L.A.S.E.R. source to emit a minimum value of L.A.S.E.R. energy necessary to form a gas bubble in at least one elementary area extending in a cutting plane of an ocular tissue, wherein the method comprises executing, by a data processing unit:
   a) Receiving a reference image of the ocular tissue, wherein the reference image is an Optical Coherence Tomography (OCT) image, said reference image having been acquired by an imaging system prior to the emission of a plurality of L.A.S.E.R. beams able to focus at least at one sampling point of each elementary area, each L.A.S.E.R. beam having a respective energy different from the other L.A.S.E.R. beams of the plurality of L.A.S.E.R. beams,
   b) Receiving at least one current image of the ocular tissue, wherein the at least one current image is an OCT image, each current image having been acquired by the imaging system subsequently to the emission of at least one L.A.S.E.R. beam of the plurality of L.A.S.E.R. beams,
   then for each elementary area, implementing:
   c) Detecting at least one gas bubble formed in the elementary area by comparing the reference image with each current image, each gas bubble being associated with a respective L.A.S.E.R. beam, wherein the step of detecting comprises, for each current image:
      calculating, for each sampling point, an intensity variation of backscattered light received by the imaging system between the pixels of the respective current image and the pixels of the reference image, and
      comparing this calculated intensity variation with a threshold value to identify the formation of a gas bubble if the calculated intensity variation is greater than the threshold value,
   d) Determining based on the at least one detected gas bubble, a minimum value of energy necessary for the formation of a gas bubble in the elementary area, and
   e) Causing the femtosecond L.A.S.E.R. source to emit radiation with the determined minimum value of energy.

2. The method according to claim 1, wherein for each elementary area, each L.A.S.E.R. beam is focused at a single sampling point of the elementary area, the receiving step b) comprising receiving a plurality of current images of the ocular tissue, each current image having been acquired by the imaging system subsequently to the emission of a respective L.A.S.E.R. beam in each elementary area.

3. The method according to claim 2, wherein for each elementary area:
   if a single gas bubble is detected:
      assigning to the minimum value a multiple k of the energy of the L.A.S.E.R. beam having induced the formation of the detected gas bubble, k being a decimal number comprised between 1 and 2,
   if several gas bubbles are detected:
      selecting among the current images in which a gas bubble is detected, the current image associated with the L.A.S.E.R. beam of the lowest energy, and
      assigning to the minimum value a multiple k of the energy of the L.A.S.E.R. beam associated with said selected current image, k being a decimal number comprised between 1 and 2.

4. The method according to claim 1, wherein for each elementary area, each L.A.S.E.R. beam is focused at a respective sampling point of the elementary area, the receiving step b) comprising receiving a current image of the ocular tissue, said current image having been acquired by the imaging system subsequently to the emission of the plurality of L.A.S.E.R. beams at a respective sampling point of each elementary area.

5. The method according to claim 4, wherein for each elementary area:
   if a single gas bubble is detected:
      assigning to the minimum value a multiple k of the energy of the L.A.S.E.R. beam associated with the sampling point at which the gas bubble is detected, k being a decimal number comprised between 1 and 2,
   if several gas bubbles are detected:
      selecting among the sampling points at each of which a gas bubble is detected, the sampling point associated with the L.A.S.E.R. beam of lowest energy, and
      assigning to the minimum value a multiple k of the energy of the L.A.S.E.R. beam associated with said selected sampling point, k being a decimal number comprised between 1 and 2.

6. The method according to claim 1, further comprising:
   f) recording by the data processing unit the minimum value determined for each elementary area in a storage unit.

7. The method according to claim 6, wherein the ocular tissue comprises a set of elementary areas extending in a plurality of cutting planes each containing at least one elementary area, the method comprising the reiteration of steps a) to e) for each cutting plane in order to determine a three-dimensional map of the minimum values of energy necessary for the formation of gas bubbles in the set of the elementary areas of the ocular tissue.

8. A device for causing a femtosecond L.A.S.E.R. source to emit a minimum value of L.A.S.E.R. energy necessary to form a gas bubble in at least one elementary area extending in a cutting plane of an ocular tissue, the device including:
   an imaging system for the acquisition of images; and
   a data processing unit configured to execute a method comprising:
   a) Receiving a reference image of the ocular tissue, wherein the reference image is an Optical Coherence Tomography (OCT) image, said reference image having been acquired by the imaging system prior to the emission of a plurality of L.A.S.E.R. beams able to focus at least at one sampling point of each elementary area, each L.A.S.E.R. beam having a respective energy different from the other L.A.S.E.R. beams of the plurality,
   b) Receiving at least one current image of the ocular tissue, wherein the at least one current image is an OCT image, each current image having been acquired by the imaging system subsequently to the emission of at least one L.A.S.E.R. beam of the plurality of L.A.S.E.R. beams, then for each elementary area:

c) Detecting at least one gas bubble formed in the elementary area by comparing the reference image with each current image, each gas bubble being associated with a respective L.A.S.E.R. beam, wherein the step of detecting comprises, for each current image:

calculating, for each sampling point, an intensity variation of backscattered light received by the imaging system between the pixels of the respective current image and the pixels of the reference image, and comparing this calculated intensity variation with a threshold value to identify the formation of a gas bubble if the calculated intensity variation is greater than the threshold value, d) Determining, based on the at least one gas bubble, a minimum value of energy necessary for the formation of a gas bubble in the elementary area, and e) Causing the femtosecond L.A.S.E.R source to emit radiation with the determined minimum value of energy.

9. The device according to claim 8, wherein for each elementary area, each L.A.S.E.R. beam is focused at a single sampling point of the elementary area, and the method comprises receiving a plurality of current images of the ocular tissue, each current image having been acquired by the imaging system subsequently to the emission of a respective L.A.S.E.R. beam in each elementary area.

10. The device according to claim 9, wherein the method comprises, for each elementary area:

if a single gas bubble is detected:

assigning to the minimum value a multiple k of the energy of the L.A.S.E.R. beam having induced the formation of the detected gas bubble, k being a decimal number comprised between 1 and 2, if several gas bubbles are detected:

selecting among the current images in which a gas bubble is detected, the current image associated with the L.A.S.E.R. beam of lowest energy, and assigning to the minimum value a multiple k of the energy of the L.A.S.E.R. beam associated with the selected current image, k being a decimal number comprised between 1 and 2.

11. The device according to claim 8, wherein for each elementary area, each L.A.S.E.R. beam is focused at a respective sampling point of the elementary area, the method comprising receiving a current image of the ocular tissue, said current image having been acquired by the imaging system subsequently to the emission of the plurality of L.A.S.E.R. beams at a respective sampling point of each elementary area.

12. The device according to claim 11, wherein the method comprises, for each elementary area:

if a single gas bubble is detected:

assigning to the minimum value a multiple k of the energy of the L.A.S.E.R. beam associated with the sampling point at which the gas bubble is detected, k being a decimal number comprised between 1 and 2, if several gas bubbles are detected:

selecting among the sampling points at each of which a gas bubble is detected, the sampling point associated with the L.A.S.E.R. beam of lowest energy, and assigning to the minimum value a multiple k of the energy of the L.A.S.E.R. beam associated with said selected sampling point, k being a decimal number comprised between 1 and 2.

13. The device according to claim 8, the method further comprising recording the minimum value determined for each elementary area in a storage unit.

14. The device according to claim 13, wherein the ocular tissue comprises a set of elementary areas extending in a plurality of cutting planes each containing at least one elementary area, the method further comprising reiterating steps a) to e) for each cutting plane in order to determine a three-dimensional map of the minimum values of energy necessary for the formation of gas bubbles in the set of the elementary areas of the ocular tissue.

15. A method for causing a femtosecond L.A.S.E.R. source to emit a minimum value of L.A.S.E.R. energy necessary to form a gas bubble in an elementary area extending in a cutting plane of an ocular tissue, wherein the method comprises:

acquiring a reference image of the ocular tissue, wherein the reference image is an Optical Coherence Tomography (OCT) image;

emitting, after acquiring the reference image, a plurality of L.A.S.E.R. beams, wherein each L.A.S.E.R. beam of the plurality of L.A.S.E.R. beams is focused on a different sampling point of the elementary area, and wherein each L.A.S.E.R. beam of the plurality of L.A.S.E.R. beams has a different energy value from the other L.A.S.E.R. beams of the plurality of L.A.S.E.R. beams;

acquiring, after emitting the plurality of L.A.S.E.R. beams, a current image of the ocular tissue, wherein the current image is an OCT image;

detecting at least one gas bubble formed in the elementary area by comparing the reference image with the current image, each detected gas bubble being associated with a L.A.S.E.R. beam of the plurality of L.A.S.E.R. beams, wherein the detecting comprises:

calculating, for each sampling point of the elementary area, an intensity variation of backscattered light between the pixels of the current image and the pixels of the reference image, comparing this calculated intensity variation with a threshold value, and identifying the formation of a gas bubble at a sampling point if the calculated intensity variation for that sampling point is greater than the threshold value;

determining based on the at least one detected gas bubble, a minimum value of energy necessary for the formation of a gas bubble in the elementary area; and causing the femtosecond L.A.S.E.R. source to emit radiation with the determined minimum value of energy.

16. The method according to claim 15, wherein determining the minimum value of energy comprises identifying which L.A.S.E.R. beam has the lowest energy value of the plurality of L.A.S.E.R. beams that caused a gas bubble to form.

17. The method according to claim 16, wherein determining the minimum value of energy further comprises multiplying the lowest energy value by a predetermined multiple.

* * * * *